United States Patent [19]

Kell

[11] Patent Number: 5,776,783

[45] Date of Patent: *Jul. 7, 1998

[54] METHOD OF MONITORING THERAPEUTIC AGENT CONSUMPTION

[75] Inventor: Michael Kell, Atlanta, Ga.

[73] Assignee: Private Clinic Laboratories, Inc., Atlanta, Ga.

[*] Notice: The term of this patent shall not extend beyond the expiration date of Pat. No. 5,547,878.

[21] Appl. No.: 715,016

[22] Filed: Sep. 17, 1996

Related U.S. Application Data

[60] Continuation-in-part of Ser. No. 675,863, Jul. 5, 1996, Pat. No. 5,652,146, which is a division of Ser. No. 248,102, May 24, 1994, Pat. No. 5,547,878, which is a continuation-in-part of Ser. No. 145,821, Nov. 2, 1993.

[51] Int. Cl.$^6$ ................................................ G01N 33/48
[52] U.S. Cl. ........................... 436/111; 436/808; 436/901
[58] Field of Search .................................. 436/111, 171, 436/808, 901

[56] References Cited

U.S. PATENT DOCUMENTS

| | | |
|---|---|---|
| 2,564,247 | 8/1951 | Carson et al. . |
| 3,856,469 | 12/1974 | Schneider et al. ................... 234/230 |
| 3,901,655 | 8/1975 | Shukla et al. . |
| 4,104,367 | 8/1978 | Gomez et al. . |
| 4,196,185 | 4/1980 | Focella et al. . |
| 5,047,329 | 9/1991 | Suzuki ................................ 435/18 |
| 5,137,692 | 8/1992 | Fritz ................................... 422/61 |
| 5,179,027 | 1/1993 | Fisher ................................. 436/56 |
| 5,547,878 | 8/1996 | Kell .................................... 436/111 |

OTHER PUBLICATIONS

Balabanova, et al., Methadone distribution in blood, cerebrospinal fluid, urine and organ tissues, Embase No. 92091431, Austria 1991.

Nilsson et al., Effect of Urinary pH on the disposition of methadone in man, Embase No. 82171209, W. Germany 1982.

Primary Examiner—Lyle A. Alexander
Attorney, Agent, or Firm—Kennedy, Davis & Kennedy, P.C.

[57] ABSTRACT

Quantitative compliance markers and associated methods for monitoring patient compliance with medication prescriptions associated with compliance markers have been found to eliminate the need for specific quantitative relationships for each new drug tested. Such compliance markers and methods for monitoring patient compliance utilize pharmacologically inert substances, namely the weak acids benzodiazepines, or non-metabolizable substances in association with an underlying drug at a measurable dosage, so as to correlate compliance marker concentration with underlying medication concentration to determine amount of actual medication ingested.

20 Claims, 6 Drawing Sheets

METHOD OF MONITORING THERAPEUTIC AGENT CONSUMPTION

REFERENCE TO RELATED APPLICATION

This is a continuation-in-part of application Ser. No. 08/675,863 filed Jul. 5, 1996, now U.S. Pat. No. 5,652,146, which is a divisional application of application Ser. No. 08/248,102 filed May 24, 1994, now U.S. Pat. No. 5,547,878 issued Aug. 20, 1996, which was a continuation-in-part of application Ser. No. 08/145,821 filed Nov. 2, 1993.

TECHNICAL FIELD

The present invention relates generally to monitoring patient compliance with medication prescriptions. More particularly, the invention relates to compositions and methods for monitoring patient compliance using quantitative compliance markers in association with prescribed medications.

BACKGROUND OF THE INVENTION

In the fields of human and animal medicine, psychiatry and animal husbandry, insuring that the patient or animal ingests the proper amount of medicine, hormone or nutrient to produce a desired effect is a commonly encountered problem. For example, human research has demonstrated that patients typically ingest only half the amount of medications prescribed by their physicians. Thus, patients placed on prescribed medication treatment programs are often monitored. Both subjective and objective methods are used to identify bothersome symptoms and to implement necessary changes during the course of treatment. Monitoring generally continues for as long as treatment is provided. For example, the Hamilton Anxiety Scale can be used to quantify the amount of anxiety remaining as treatment proceeds for an anxiety-related condition. If the level of residual anxiety decreases significantly, say from the proper prescription of a benzodiazepine drug, like diazepam, then the physician and patient can be assured that treatment is efficacious and should be continued.

Preferably both quantitative and analytical methods should be used to monitor the patient on a repetitive basis to insure that the patient is indeed ingesting the prescribed amounts of medication. Currently, the most common method of monitoring patients for medication compliance is clinical observation which involves individual counseling and close personal supervision by physicians. Physicians observe physiological signs and symptoms such as intoxication, drug withdrawal typically occurring for benzodiazepines, barbiturates and opioids, or residual signs of illness such as tremor in anxiety, sighing in depression, and nociception in pain syndromes. Physicians also listen to patient complaints regarding degree of pain relief and evaluate psychological changes over time. This method however is time consuming, expensive and highly subjective. Needless to say, it is fraught with potential errors.

Additional compliance information can be obtained using qualitative urine monitoring methods such as the standard laboratory procedure called enzyme-multiplied immunoassay (EMIT). Utilizing an arbitrary cutoff value, these methods provide the clinician with a simple positive or negative indication of the possible presence or absence of a parent drug or its metabolites in a patient's urine. The parent drug is the prescribed medication itself and the metabolites are those chemical derivatives of the medication which naturally occur upon the patient's body metabolizing the medication. These tests do not provide information concerning the time or amount of last drug use or whether or not the prescribed dose of medication was ingested properly, diverted or supplemented. This type of testing fails to provide any indication as to the actual quantity of drug ingested.

Physicians utilizing only clinical evaluation and qualitative urine drug screening test results may develop problems in their treatment methods. Such is often the case in treating patients who have become biochemically dependent upon opioids either through prescription or illegal use. Opioid addicts experience great difficulty eliminating their dependency upon such drugs and typically enter into extended rehabilitative treatment programs which utilize prescribed methadone dosages to eliminate opioid dependency. For example, physicians must effectively assess the condition of patients on methadone maintenance programs in order to adjust dosages and monitor compliance. If a patient is continually testing positive for opioids or complains of continuing subjective opioid withdrawal symptoms, a physician may conclude that the currently prescribed dose of methadone is not sufficient to curb the body's desire for opioids and may increase the prescribed dosage. This highly subjective monitoring method can result in over-medication with patients being given more methadone than they require, creating an unnecessary reliance on methadone. Alternately, physicians sometimes conclude, erroneously, that a patient's methadone dose is sufficient to prevent opioid withdrawal and drug cravings and deny the patient a further increase sufficient to stop illicit opioid use. Such action can expose the patient to further intravenous drug use and the associated negative social and medical consequences which can follow such as HIV, hepatitis, and blood poisoning.

Similar problems with treatment may arise for patients prescribed diazepam for longstanding generalized anxiety. Patients may not show improvement in their condition even though this therapy is known to be highly efficient. This medication is a member of the sedative-hypnotic family of benzodiazepines which have been clinically shown to cause sedation, hypnosis, decreased anxiety, muscle relaxation, anterograde amnesia and anticonvulsant activity. A patient, for example, may insist that he or she is ingesting the medication as prescribed, and yet claim no significant improvement in symptomology. The physician suspects that the patient is not ingesting the medication properly and perhaps is selling it, and orders a qualitative urine drug screen to verify compliance. The screen is reported as positive at greater than 200 ng/ml drug concentration. Since some benzodiazepine is present the physician assumes, incorrectly, that the patient is compliant, but will require additional medication and increases the daily dose. In truth, the patient is diverting the majority of his or her dose to the illicit market and only ingesting enough drug to test positive on the drug screen.

Patients also commonly visit multiple physicians to obtain similar medication for self-ingestion. These patients desire the intoxicating effects of the medication, but are unable to obtain sufficient quantities from a single source. Qualitative tests like the EMIT are generally not useful in detecting this situation since the quantitative amount of medication concentration in the body is not measured.

Another monitoring method sometimes used, though most often only in research centers, is direct measurement of parent drug concentrations or active metabolites concentrations of the drug in plasma. This method has been particularly useful to eliminate illicit opioid use of patients on methadone maintenance programs. It is known from analytical studies using venous blood samples obtained from stable patients that plasma methadone concentrations ranging from 150–600 ng/ml are necessary. This direct method of testing is not very practical since it requires the use of time consuming, expensive, and highly technical analytical procedures such as high pressure liquid chromatography and gas chromatography/ mass spectrometry since active and inactive metabolites must be quantified separately. Additionally, for many patients the obtaining of plasma samples is invasive, offensive and difficult due to inadequate venous access. Medical professionals must also be concerned about their own health safety in doing this since they are exposed to blood products from patient groups which can have a high prevalence of hepatitis and HIV infection. Therefore, such procedures are primarily conducted in research centers and not generally utilized in standard maintenance programs.

Another problem commonly encountered by pharmaceutical companies occurs whenever they are comparing the clinical efficacy of a potential, new medication versus a placebo. For example, in clinical trials new medications appear to be two to three times as effective as a placebo, i.e., placebo response rates can range from 20–30% while drug response rates range from 60–80%. One explanation for why new medications are not more effective is that many test subjects are not taking their prescribed doses. The end result is that many medications with undesirable side-effects, as formulated for the study, may appear not to be efficacious and be inappropriately dropped from research only because subjects are not ingesting sufficient drug to observe the desired effects. Other medications may end up being clinically prescribed at higher doses than necessary, increasing morbidity and mortality, because the researchers think the subjects are taking more medication than they actually are.

Researchers have proposed several solutions to this problem. For instance, drug compliance in a research setting has been monitored by counting the residual pills remaining following a course of treatment. In this regard the use of a tablet container which incorporates a recorder that records each opening of the container is described in the scientific literature. However, the technique of residual pill counting is not necessarily indicative of pill ingestion.

Another method of drug compliance monitoring which is disclosed in scientific literature involves adding secondary substances to medication which presence can be qualitatively detected in blood work and other bodily fluids. In this regard, some researchers have added ingredients like riboflavin to pills and looked for the ingredient in the patient's serum, urine, or feces. However, testing serum necessitates additional labor and care since it requires a blood sample to be taken. Furthermore, since ingredients like riboflavin are commonly found in food, beverage, and multivitamins, they are normally also present in urine independent of any supplemented riboflavin. The normal presence of such ingredients in the urine therefore leads to false positive readings during testing. Additionally, no accurate relationship has been determined between the presence of these markers in the urine and the amount of medication taken.

As an alternative solution, researchers have added relatively harmless amounts of a second medication to pills for this purpose. However, the addition of this type of ingredient again only indicates that patients are taking some pills. Depending on the half-life of these secondary medications, researchers may only be able to tell if the patient ingested the medication recently. Furthermore, research with "second medication" type markers has focused on serum testing for verification.

While methods now exist for determining compliance using quantitative urine monitoring that are useful for insuring that patients are obtaining adequate body levels of specific drugs, as disclosed in the applications earlier cited, these methods require the development of specific analytical methods tailored for measuring each specific drug and its metabolites. Often these methods are not available in a clinically useful manner in the early development of new drugs.

While providing useful information relative to patient status and treatment compliance, the clinical monitoring methods described above, i.e. clinical interviews with patients, direct plasma drug measurement, qualitative urine drug screening, residual tablet counting, and quantitative urine drug screening for each drug ingested, each have distinct drawbacks which limit their usefulness in experiments and treatment plans. Therefore, it is seen that a need remains for a predictable method of monitoring patients who have been placed on potentially abusable and dangerous maintenance medications or new experimental drugs for compliance therewith. A need remains for a method of monitoring drug ingestion which is not invasive to the patient and which does not require a predetermined mathematical relationship specific for each drug being monitored. To help prevent continued medication misuse and better optimize patient medication dose, it would be advantageous for patients to have a facile bodily fluid, such as urine, regularly and quantitatively monitored for the presence of the medication. It would be further desirable not to have to rely on the distinctive pharmacokinetics of each medication in such monitoring but on the pharmacokinetics of only a standard compliance marker or a series of compliance markers. Such a monitoring method would help physicians both in prescribing adequate doses of medication and in monitoring patients to insure that they were ingesting the prescribed amounts. Obtaining a fluid sample like urine would not be invasive to the patient or a safety risk to the health care provider.

Furthermore, a need remains for a composition which includes an easily measurable quantitative compliance marker and a therapeutic agent, in which the consumption compliance marker readily passes through the renal system with little or no pharmacological effect on the patient. Accordingly, it is to the provision of such improved methods and compositions that the present invention is primarily directed.

SUMMARY OF INVENTION

A composition and method has been developed for particular use in clinical drug evaluation studies for tracking compliance of patients on prescription medications (therapeutic agents) by using compliance markers (quantitative consumption markers) in association with the medications, which consumption compliance marker concentrations can be accurately measured in the urine. Upon a determination of the compliance marker concentration, a correlation is made to the amount of actual medication ingested. Only a small number of mathematical relationships need be determined between marker intake and urine output, rather than developing unique relationships for each and every drug tested. Moreover, quantitative relationships exist between the amount ingested and the amount appearing in the urine as a function of physical parameters such as patient weight, lean body mass, age, urine pH, urine specific gravity (which may be measured by a refractometer, hydrometer or chemical methods), or other equivalent parameters related to dissolved urinary solids such as urine osmolality. This is especially useful in clinical trials of new, potentially useful medications.

It has now been discovered that pharmacologically inert quantities of weakly acidic medications*, specifically benzodiazepines, provide quantitative compliance markers in association with therapeutic agents. The measurable benzodiazepines and their metabolites readily pass through the renal system into the urine making benzodiazepines and substances with similar properties especially suitable as compliance markers. Preferably a pharmacologically inert quantity of a benzodiazepine, referred to as a "quantitative compliance marker," is added to each unit dose of therapeutic agent, i.e. medication, hormone or nutrient, which quantitative compliance marker concentration can be measured in the urine. For the purposes of this application, an inert substance shall include biologically inactive substances which are non-metabolizable and pharmacologically insignificant amounts of therapeutic drugs and their metabolites, which can still be detected in the urine of a patient.

*weak acids are gradually defined by acid disasociation reactions with an acid disasociation construct<1.

The quantitative compliance marker may be added to a medical formulation by being mixed homogeneously throughout the formulation or solution, or as a film or coating on a tablet or capsule containing the formulation. Additionally, the marker may be introduced as particulates in a suspension. If more than one medication has been prescribed, a separate quantitative compliance marker may be used in association with each medication. Preferably the quantitative compliance markers have biological half-lives of between 24 and 48 hours so that they will appear in a urine sample long after ingestion. The quantitative compliance markers are associated with therapeutic agents at a predetermined proportion and preferably at a sufficiently small dosage to insure the absence of psychotropic and physiological effects on the patient.

In the method of monitoring therapeutic agent consumption, random samples of a patient's urine may be analyzed for the concentration of a quantitative compliance marker associated with a therapeutic agent. The concentration of the quantitative compliance marker then serves as the basis for both monitoring consumption compliance with the prescribed therapeutic agent dosage and to establish the proper medication dosage.

In the method of monitoring therapeutic agent consumption, if appropriate, it is first determined whether the urine sample is adulterated as by comparing urine pH, specific gravity, and creatinine level with that of a normal urine sample and the specific values previously determined for the patient. If found to be unadulterated, and probably from the patient being monitored, the raw urine compliance marker concentration is measured along with the urine specific gravity or urine osmolality.

Once the actual concentration of the compliance marker in the sample is determined (the raw urine compliance marker concentration), adjustments are made to account for the affects of variations in certain urinary parameters upon this concentration, by adjusting for the compounding effects of urine specific gravity. This is accomplished by accounting for the difference between the measured specific gravity and a reference specific gravity. An adjustment is also made to reflect a normalization to a constant patient body weight such as 70 kg or 154 lbs. This final adjusted compliance marker concentration is defined as the normalized urine compliance marker concentration. In the alternative, the normalized urine compliance marker concentration may be calculated as a function of the urine osmolality, the measured raw urine compliance marker concentration and the patient body weight normalized to a constant value.

The normalized urine compliance marker concentration value is then used to determine whether the patient is compliant by comparing the value of the normalized compliance marker concentration to an expected value, for the purpose of determining whether there is any significant statistical variance between the two values. By obtaining multiple urine samples from the patient, once or twice a week, it is possible to establish an expected baseline normalized compliance marker concentration against which a current or future value can be statistically compared. An expected baseline compliance marker concentration for a patient is the mean normalized compliance marker concentration from historical values obtained from the patient. This method of monitoring compliance is dependent upon the assumption that the patient is initially compliant in order to get the expected value. In the alternative, expected ranges of normalized compliance marker concentrations for specific compliance marker dosages, may be used for comparison. These ranges are based on a patient database independent of the subject patient.

A corresponding value for the actual medication dose ingested is then calculated by multiplying the prescribed medication dose with the calculated normalized urine compliance marker concentration, and dividing the product by the expected normalized urine compliance marker concentration.

DETAILED DESCRIPTION

Specifics of Composition

Figure 1:
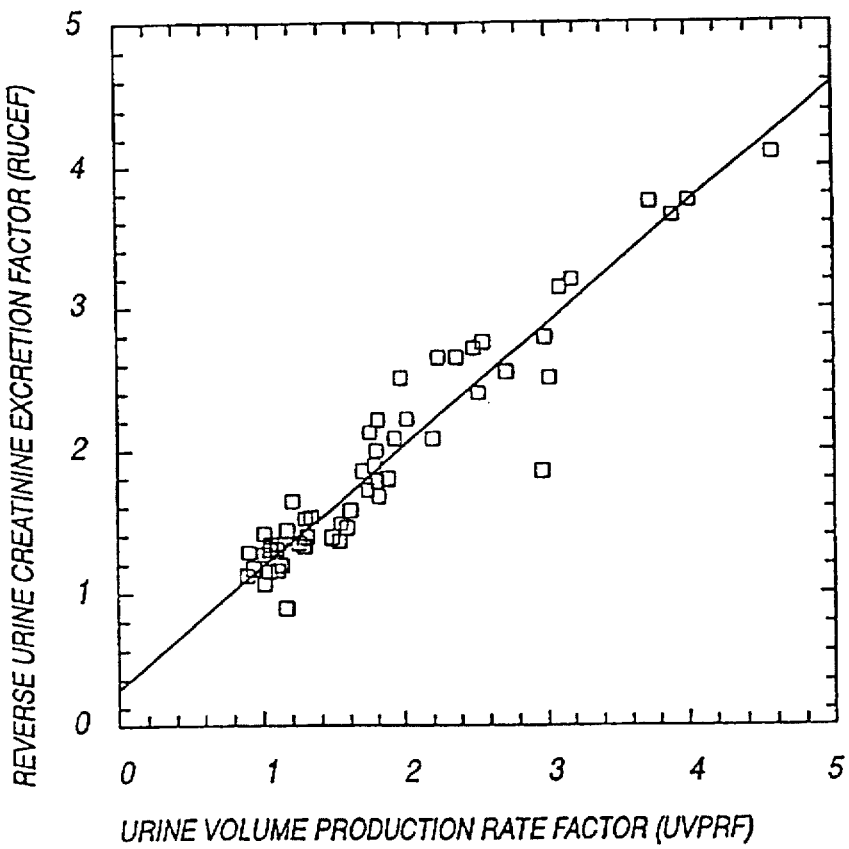
FIG. 1 is a graph of reverse urine creatinine excretion factor (RUCEF) versus urine volume production rate factor (UVPRF) showing their substantially linear relationship.

A specified amount of the quantitative compliance marker benzodiazepine is added to each unit dose of therapeutic agent, i.e. medication, hormone or nutrient, which marker can be measured in the urine. For the purposes of this application, an inert substance includes biologically inactive substances which are non-metabolizable, and pharmacologically insignificant amounts of therapeutic drugs and their metabolites, which can still be detected in the urine of a patient. Preferably the inert substances are not normally found in urine and are not normally ingested as food or drink or as a medicine. Also the inert substances are preferably weak acids so that they are unaffected by urine pH and pass through the renal system without resorption. Additionally, there are mathematical relationships between weak acids with pK (dissociation constants) values less than 4, and their individual active and inactive metabolites.

Benzodiazepines, such as the alprazolam Xanax and the diazepam Valium, which are normally prescribed as therapeutic agents for treatment of anxiety related conditions, are especially suited as markers because their urinary excretion is not dependent upon urine pH, as are weak bases, because they are completely ionized at the typical urine pH range of 4.5–8.5. This insures complete clearance after glomerular filtration in the kidneys, since these drugs are not absorbed or secreted in great quantities by the renal tubules of the kidneys. For instance, Valium could serve as a marker at a dosage range of 1–10 mg a day, depending on the individual patient.

Advantageously, while many hepatic metabolites of benzodiazepine family of medications are absorbed fully by the digestive tract, being very lipophilic in neutralized form, they are not significantly further metabolized by the liver. Consequently, simple relationships exist between oral intake and urine output, as corrected for patient weight and urine specific gravity. Moreover, if the compounds are psychotropically and physiologically inactive at low doses, their ingestion will not adversely affect the patient. Therefore it is preferable that pharmacologically inert quantities of a benzodiazepine be used as a marker.

A benzodiazepine quantitative compliance marker may be added to a medical formulation by being mixed homogeneously throughout the formulation or as a film or coating on a tablet or capsule containing the formulation. Additionally, the marker may be mixed in a solution or introduced as particulates in a suspension. If more than one medication has been prescribed, a separate quantitative compliance marker may be used in association with each medication. Preferably the markers have biological half-lives of between 24 and 48 hours so that they will appear in a urine sample long after ingestion.

A general example using this type of quantitative compliance marker, is the following:

A clinical examination shows that a patient needs to ingest three pills of medication a day. If 0.5 mgs of a long-acting inactive metabolite of alprazolam or diazepam (having plasma half-lives greater than 24 hours) is added to each pill as a compliance marker, each compliant patient will have a specified and constant amount of the compliance marker in each urine sample. The average amount measured, as normalized for urine specific gravity, and a constant patient body weight, will be directly related to the number of pills ingested, for instance 120 concentration units assuming each pill contains 40 concentration units. Persons taking only 2 pills will have 80 concentration units, and persons taking only 1 pill will have 40 concentration units. Having this data, a pharmaceutical company can then create dose-response curves for the drug since they will have patients taking different amounts of drugs due to variations in compliance.

A second general example is the following:

A quantitative compliance marker is used in a methadone concentrate at a constant ratio, i.e., one compliance marker per ten methadone. Therefore the amount of methadone ingested will be proportional to the amount of compliance marker taken. Consequently, taking less or more methadone than prescribed will show up as less or more marker in the urine, thus helping to eliminate diversion of a drug to a second individual or supplementing of a patient's drug intake from another source. In this way a number of distinct markers may be used to monitor the compliance of a variety of medications.

Other inert substances may also serve as markers in the following method of monitoring consumption compliance with therapeutic agents. For example, the barbiturate phenobarbital may be used as a compliance marker in conjunction with other prescribed medications, providing the dosage of the compliance marker is low, and there is no drug cross-reactivity with the prescribed medication or other medication that the patient is currently taking.

Specifics of Method

A patient is initially prescribed a medication and dose based on several factors. These ordinarily include the severity and duration of illness, amounts and types of medications previously used, current or previous physiological and/or physical dependence upon other prescription or illicit drugs, previous medical history, patient sex, pregnancy status, patient weight and ingestion of other therapeutic medications. Often medication dose is adjusted upwardly until a patient no longer complains of residual signs and symptoms of his or her psychiatric and/or medical illness, is no longer experiencing withdrawal signs and symptoms if on a medication-replacement taper to abstinence program, or loses his or her desire to use illicit medications if a substance abuse problem exists. Medication dose is increased per published and accepted standard medical protocols for each family of psychiatric and medical drug, usually "x" mg every few days. A compliance marker is associated with the prescribed medication at a preestablished ratio so that as the patient takes his/her prescription, he/she also takes a correlative amount of the compliance marker.

Testing for Adulteration

In certain circumstances it may be appropriate to first test for adulteration of urine samples. Such a circumstance may be appropriate in drug rehabilitation/addiction treatment settings. If this is necessary, a supervised, spot sample of urine should be first collected from a patient. The urine sample is collected by simply providing the patient with a standard urine collection bottle into which he or she can urinate. Alternatively, a sample can be collected by catheterization or withdrawn from a urine collection bag. Only several milliliters of urine are required for analysis. With this sampling method, it is not necessary to record the volume collected or completely void the bladder. Loss of a portion of the sample is also not detrimental as long as a sufficient sample remains for analysis.

Several properties of the urine are measured to evaluate whether the urine is adulterated, adulteration being the altering by a patient of his or her urine in an effort to prevent detection of illicit drug use or diversion of a drug. Adulteration typically is accomplished by adding foreign substances to the urine such as salt, bleach, or vinegar. Many patients attempt to dilute amount of drugs in the urine sample by drinking large quantities of water or by adding water to the sample. Adulteration may also occur by substituting another person's urine for the patient's own urine, including instillation of foreign urine into the patient's bladder.

In checking for adulteration, urine pH is measured, as with the use of a pH Data Logger type meter available from Oakton, to see if it is within the normally expected pH range of 4.5 to 8.5. Urine specific gravity is also measured to see if it is within the normal range of 1.004 to 1.035 units. A Digital Urinometer by Biovation may be used for this test. Creatinine, an end product of glycine and arginine metabolism excreted through the kidneys, is measured to evaluate renal function. The creatinine level in human urine usually ranges from 8 to 500 mg/dl, the range being affected by variables such as age, sex, diet, lifestyle and geographic location. Creatinine levels generally are homeostatically maintained by the body at a constant value for each individual patient over his or her lifetime. Creatinine levels may be determined on many different analyzers, including a TDx REA Creatinine System available from Abbott Laboratories. All of these tests are helpful in establishing normally expected ranges for each patient and the overall population of patients.

Once pH, specific gravity, and creatinine level values for the spot urine sample are obtained for a particular patient, comparisons can be made between the sample in question and values previously measured (if already available) both for the patient and for normals to ascertain whether the urine sample is adulterated. If no adulteration is found, a data base is created or extended for the patient so that a basis of comparison exists for future spot urine samples. Of the three measures, urinary creatinine level is generally the most useful indicator as to whether the spot sample is that of the patient or of someone else. If it is not necessary to test for adulteration of urine samples, then random urine samples are simply obtained from the patient to be analyzed in the following manner.

Measurement of Specific Gravity or Osmolality

Once a representative urine sample has been obtained, specific gravity (SG) is measured for the urine at room temperature, (22–23 degree C.) which typically ranges from 1.004 to 1.035 for normal urine. A Digital Urinometer by Biovation may be used for this test. Occasionally, urine samples may exhibit artificially elevated specific gravity values. This situation occurs whenever the urine contains a significant amount of protein, such as in the nephrotic syndrome, and/or glucose, as in diabetes mellitus. Occasionally, this can also occur when urinary cleared, radiopaque dyes are used for diagnostic purposes.

Osmolality measurement may therefore be preferred in lieu of specific gravity measurement in order to avoid these inflated values, since osmolality values are less dramatically affected by the presence of glucose and protein in the urine, and since there is a recognized relationship in scientific literature that exists between urine osmolality and urine specific gravity. Furthermore, osmolality values are not sensitive to temperature variations as are specific gravity values.

Measuring Raw Urine Compliance Marker Concentration

The unadulterated sample is next analyzed for raw urine compliance marker concentration, preferably using fluorescence polarization immunoassay (FPIA) technology. In this regard an Abbott TDX or ADX Analyzer may be profitably employed. Other standard analytical methods may also be used such as chromatography or other types of immunoassay. The value, u, obtained is the raw urine compliance marker concentration expressed in ng/ml. If appropriate, the value u includes the compliance marker metabolite concentration in the urine as well. Metabolites are those substances which result from the body's metabolism of the compliance marker.

The raw urine compliance marker concentration, u, is next converted to a normalized urine compliance marker concentration, nu, as discussed below. A historical database is then created for these values.

Calculating Normalized Urine Compliance Marker Concentration

Parameters of a patient's urine, such as pH and specific gravity, vary from one day to the next dependent upon the type and quantities of foods and beverages ingested. Additionally, individuals metabolize endogenous substances, as well as medications, at different rates. Due to variations in these daily urine parameters, concentration levels for creatinine, other endogenous compounds, and drug metabolites can vary over time. Since many endogenous compounds and drugs are weak acids under normal conditions of urine pH, significant tubular resorption does not occur and renal clearance is primarily the result of glomerular filtration. For these compounds, the major variable responsible for observed variations in urine metabolite and drug concentrations is tubular resorption or excretion of free water. The kidneys regulate urine production rates so to maintain normal blood pressure and blood osmolality. This property of the kidneys is indicated by the urine specific gravity, a physical variable relating to urinary solids and urine volume production rate. A mathematical relationship has been discovered to exist between urine compliance marker concentrations and urine specific gravity, which herein is given by the specific gravity normalized compliance marker concentration, nu.

It is now realized that renal excretion rates (mg/dl) for drugs and urine metabolites are relatively constant for any patient during a typical day. This constancy has now been experimentally verified by examining the renal excretion rates of methadone, benzodiazepines, other drugs and creatinine and other endogenous metabolites as a function of urine volume production rate. For example, sequential, complete and timed (1–8 hours holding periods) aliquots of urine for 12 compliant control subjects were collected over 24 to 72 hour periods. For each urine aliquot, urine volume production rate (ml/min), specific gravity and creatinine concentration (mg/dl) (as the tested substance) were determined. Using this data, a dimensionless, linear relationship was found to exist, that is the same for all patients, between a urine volume production rate factor (UVPRF) and a reverse urine creatinine excretion factor (RUCEF). For each individual, control, urine collection period, the UVPRF is defined by the ratio of urine volume production rate for each urine aliquot collected, v, to the urine volume production rate for the most concentrated sample in the collection period with a specific gravity usually near 1.030 (ie that specific gravity of a normal urine sample at room temperature, typical of a morning void ), v', $$UVPRF = v/v'. \qquad (1)$$

Similarly, in this example, RUCEF factor is defined by the ratio of the creatinine concentration of the most concentrated urine aliquot with a specific gravity usually near 1.030, u', to the creatinine concentration for each urine aliquot collected, u, $$RUCEF = u'/u. \qquad (2)$$

This linear relationship is shown in FIG. 1. The best fit linear regression line is given by the expression, $$RUCEF = 0.942 \cdot UVPRF + 0.121 \qquad (3)$$

$$u'/u = 0.942 \cdot v/v' + 0.121 \qquad (4)$$

where statistical evaluation results in an adjusted squared multiple R=0.985, a standard error of the estimate=0.242, and a F-ratio=4965.

Therefore, contrary to the traditional teachings of those skilled in the art, urine drug and metabolite concentrations, u, are inversely related to the volume of urine produced by the kidneys, v, clearly demonstrating that the product (u·v) is constant at any particular time point and urine pH.

Since (u·v) at any time is a constant, steady-state value, it follows that from Equation (4) some empirical mathematical relationship must exist between u and v such that given an arbitrary urine volume production rate v' and an equivalent u' at a reference point (a specific gravity of 1.030):

$$\{u \cdot v\}_{sg\ actual} = \{u' \cdot v'\}_{sg\ 1.030} \quad (5)$$

or upon rearrangement for u' gives, $$u' = u \cdot (v/v') \quad (6)$$

where the products given in Equation (6) are those measured for a spot urine sample collected with an actual specific gravity and a corrected specific gravity typical of a morning void of 1.030.

Using controlled urine collections, a urine volume production rate v' of 0.44 ml/min for persons with reasonably normal renal functions at a specific gravity of 1.030 was initially measured. A specific gravity factor is then calculated by the equation (rsg-1.000)/(msg-1.000), where rsg is the reference specific gravity, which in this case is equal to 1.030, and where msg is the measured specific gravity. The specific gravity factor is an adjustment of the measured specific gravity value to account for the difference between the measured specific gravity value and a reference specific gravity value.

Figure 2:
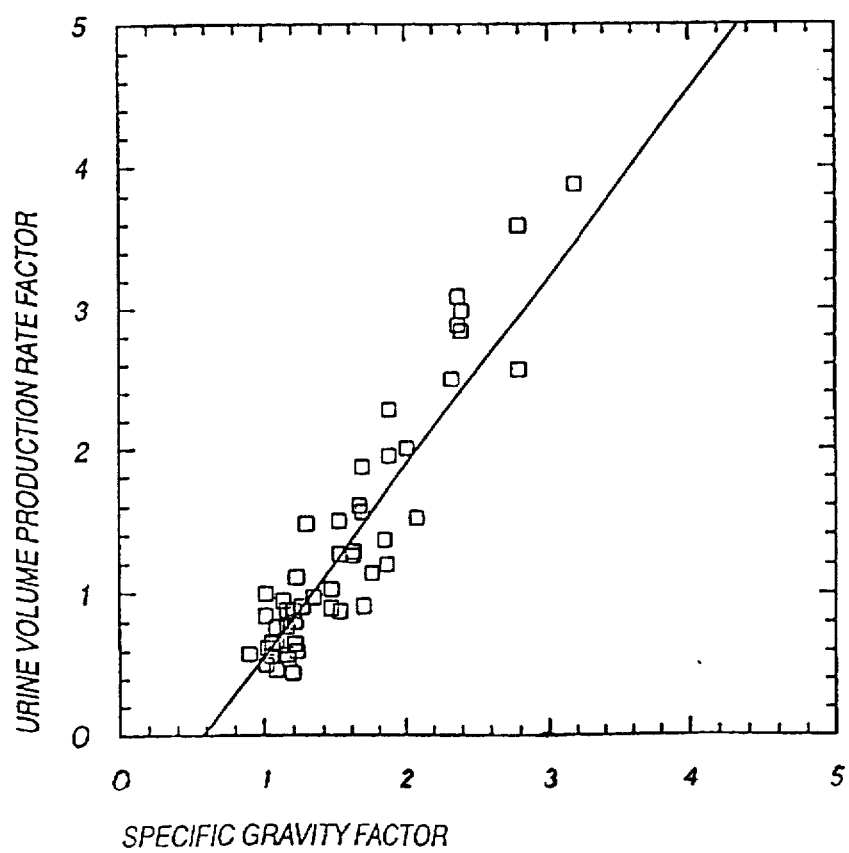
FIG. 2 is a graph of urine volume production rate factor (UVPRF) versus specific gravity factor (SGF) showing their substantially linear relationships.

It has been found that a linear relationship exists between the urine volume production rate factor and the specific gravity factor, (SGF) as shown in FIG. 2 and given as follows:

$$UVPRF = v/v' = 2.43 \cdot SGF - 1.43 \quad (7)$$

where the adjusted squared multiple R=0.856, standard error of the estimate=0.787, F-ratio=482.

Substituting Equation (7) into Equation (6) the specific gravity normalized creatinine concentration, nu, (since we are testing for creatinine) is then calculated by adjusting the actual urine creatinine concentration, u, for compounding effects of urine specific gravity at 1.030:

$$nu = u' = u \cdot (v/v') = u \cdot UVPRF = u \cdot |k_1 \cdot SGF - k_2| \quad (8)$$

wherein $k_1$ is a constant equal to 2.43 and $k_2$ is a constant equal to 1.43.

Using Osmolality Measurement In Lieu of Specific Gravity Measurement in Calculations It has been noted that specific mathematical relationships exist between the rate of urine formation (ml/min) and the concentration of creatinine in the urine. A relationship also exists between these variables and urine specific gravity. Generally, the relationships between SGF and v/v' apply to persons with normal renal function. However several situations exist in which the SGF, especially when measured by refractometry or hydrometer, is not directly related to v/v', thus creating inaccuracies in the relationships heretofore described. Such a situation occurs whenever the urine contains a significant amount of protein and/or glucose. Occasionally this can also occur whenever urinary cleared, radiopaque dyes are used for diagnostic purposes. Each of these compounds can affect the refractive index or drag coefficients for a spinning hydrometer. In situations such as these, the presence of the abnormal components results in the specific gravity value being artificially elevated. For example, protein in the urine, which is mainly albumin, causes the specific gravity to increase by about 0.003 units for every 1000 mg of protein/100 ml urine. The presence of glucose results in an increase of about 0.004 units for every 1000 mg of glucose/100 ml urine. If the presence of these influencing compounds is not considered, the specific gravity utilized in the correlation is inaccurate. This inaccuracy is readily apparent because the v/v' from the calculated SGF will fall outside of the expected range, alerting the clinician to a possible unusual situation. It will appear that the urine specific gravity is too high for the amount of urine produced. In this scenario, additional urine tests can be done to quantify the amounts of protein, glucose and radiopaque dyes. Once these figures are obtained, corrections can be applied to the calculations. For example, another urine sample can be collected after the radiopaque dye is out of the urine and numerical corrections to the refractometer or hydrometer specific gravity values can be made for protein and/or glucose. The corrected specific gravity is determined by subtraction so as to remove the effect of the abnormal urine components. Once these corrections are made, the normally expected relationships between SGF and v/v' may be noted.

However, in lieu of using SGF as a measure of urine concentrating ability, specific gravity being the mass of a unit volume of solution/mass of a unit volume of pure solvent, urine osmolality factor (hereinafter UOF) can also be used. Osmolality is the number of osmotic particles per unit volume of pure solvent. A common relationship exists in scientific literature relating urine osmolality to urine specific gravity. For instance, urine osmolality, measured in mOSM, is equal to 37500(SG-1.000). Furthermore, urine osmolality is not temperature sensitive as is urine specific gravity. The urine osmolality factor is defined as the ratio of the urine osmolality at a specific gravity of a reference point, such as 1.030, to the urine osmolality equivalent at the actual urine specific gravity. Using this equation, the following figures may be generated for protein/glucose free urines.

EXAMPLES

|  | Measured Specific Gravity | Calculated Specific Gravity Factor | Measured Osmolality | Calculated Urine Osmolality Factor |
|---|---|---|---|---|
| sample 1 | SG 1.003 | SGF 10 | Osm 112.5 | UOF 10 |
| sample 2 | SG 1.015 | SGF 2 | Osm 562 | UOF 2 |
| sample 3 | SG 1.030 | SGF 1 | Osm 1125 | UOF 1 |

It is therefore evident from this data that SGF and UOF values are equivalent and either one may be used in the application of this invention.

Refinement of the Normalized Urine Compliance Marker Equations

Independent data was gathered from 96 patients being followed in a renal disease clinic. Data available from these patients included 24 hour urine volumes, urine specific gravity, urine creatinine concentration, serum creatinine concentration, creatinine clearances measured from 24 hour collections, presence of protein and glucose in urine, urine osmolality, patient sex, age, lean body weight, total body weight, height and diagnosis.

Figure 3:
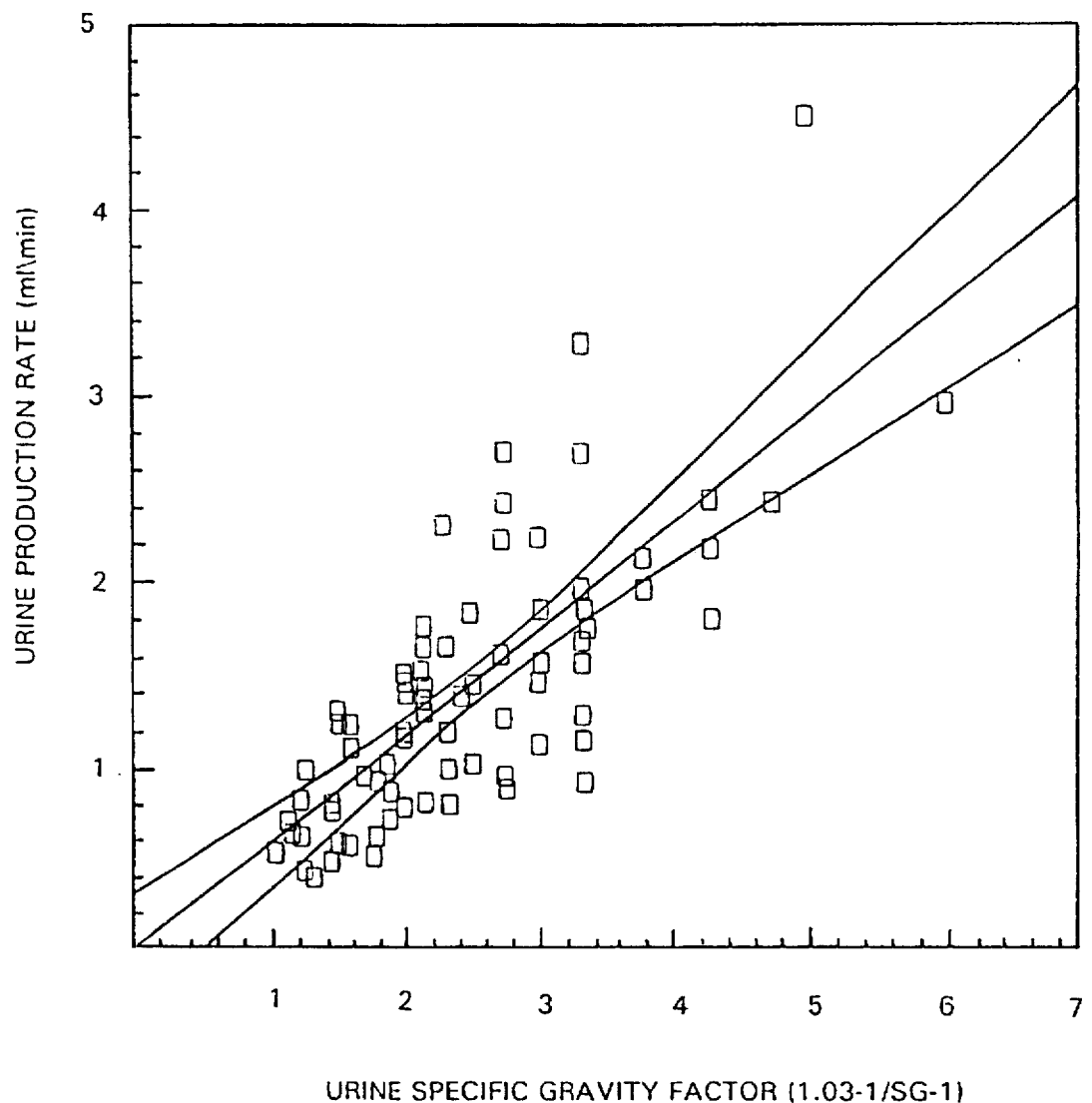
FIG. 3 is a graph of urine production rate versus urine specific gravity factor (SGF) using independent data and showing their substantially linear relationship.
Figure 4:
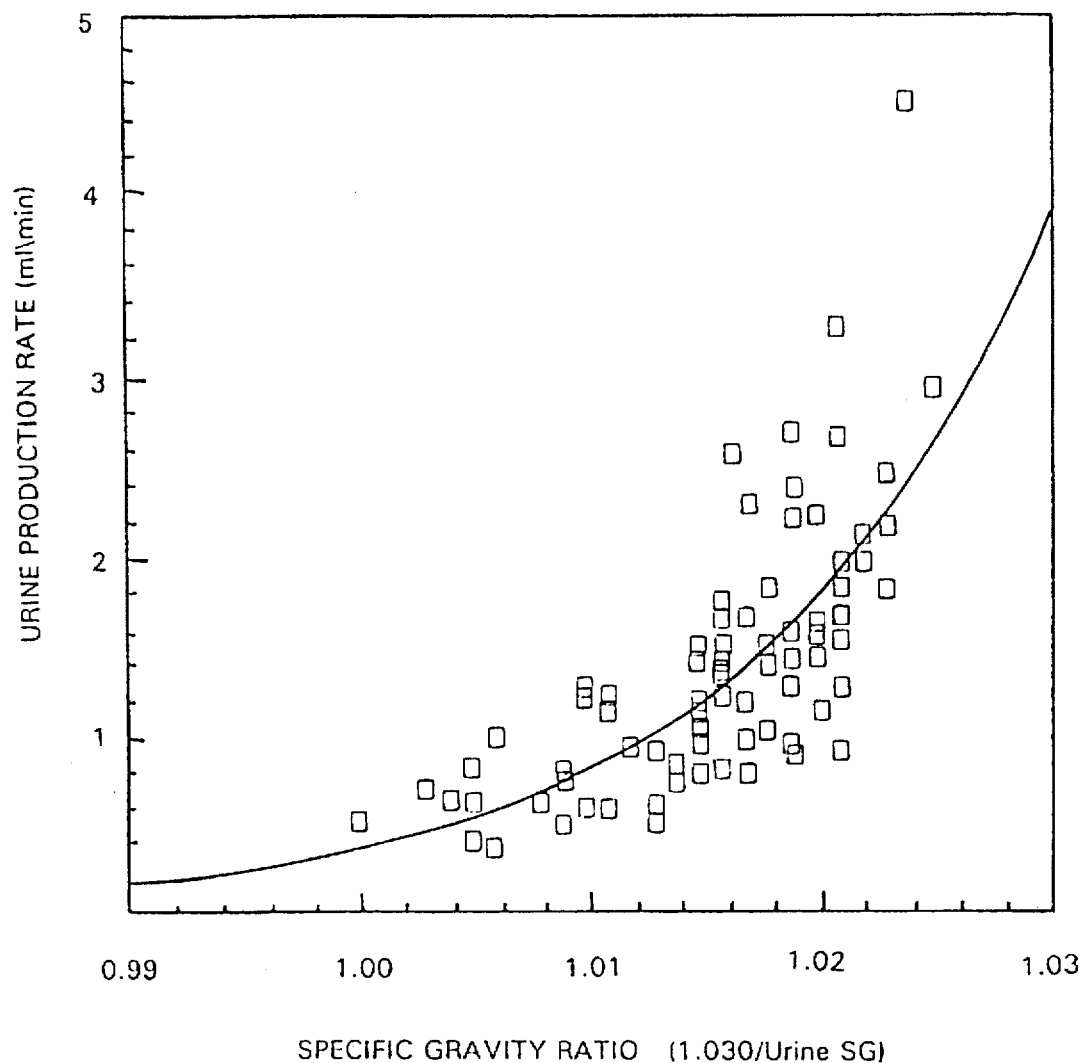
FIG. 4 is a graph of urine production rate versus specific gravity ratio (1.030/urine SG).

The independent data was first plotted by urine production rate (ml/min) versus various mathematical formulations of urine specific gravity as illustrated in FIGS. 3 and 4. Although several methods exist for plotting specific gravity or its equivalent, osmolality, on the x-axis, ie, SG ratio= 1.030/SG, SGF or even SG, the SGF and UOF relationship are preferable.

Figure 5:
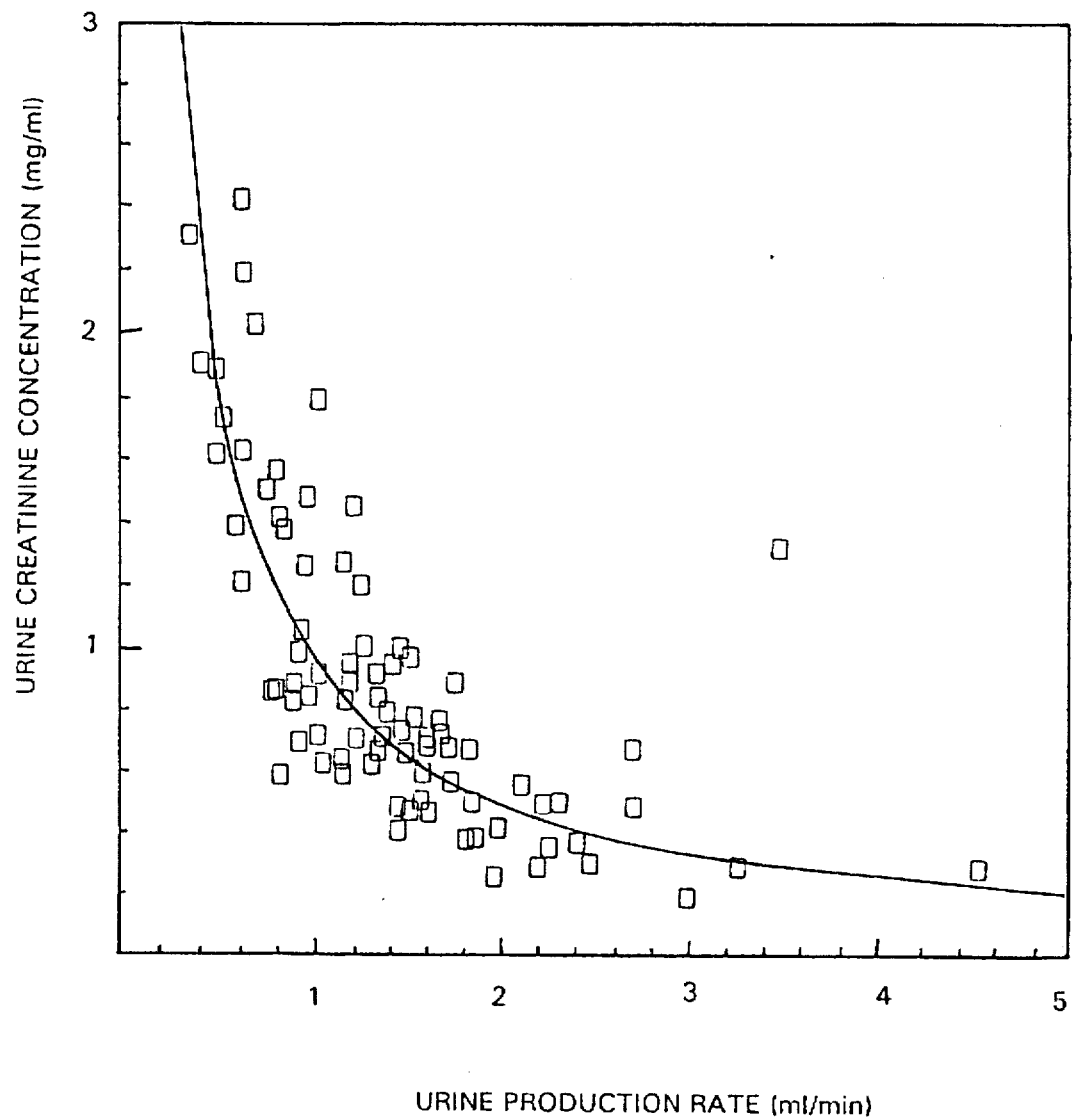
FIG. 5 is a graph of urine creatinine concentration versus urine production rate showing the inverse relationship between urine creatinine and urine production rate, forming a hyperbola.

As a further example for demonstrating in greater detail the inverse relationship between urine creatinine and urine volume production rate, urine creatinine concentration was plotted against urine production rate revealing a hyperbola in FIG. 5.

Figure 6:
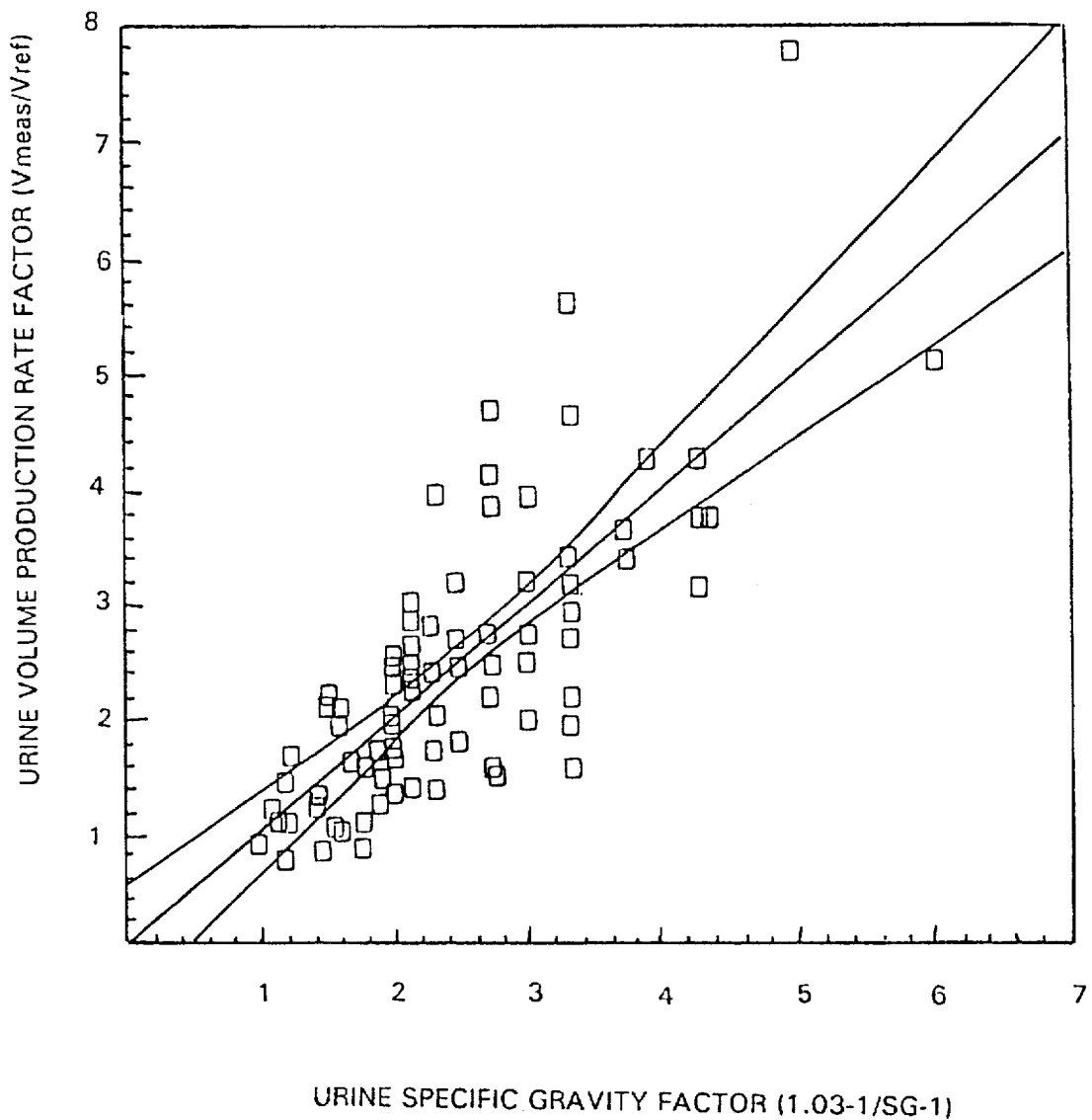
FIG. 6 is a graph of urine volume production rate factor versus urine specific gravity factor, showing a slope of one and a zero intercept and demonstrating their substantially linear relationship.

FIG. 6 plots the ratio v/v' using v' equal to 0.58 ml/min against SGF. Plotting this data gives a slope of one and a zero intercept. Data gathered from normal subjects supports this same conclusion.

These functions differ from functions described earlier in that v' is now equal to 0.58 and v is now equal to SGF·v' as compared to previous formulations where v was equal to (2.43·SGF-1.43)·v', where v' equals 0.44. The refined normalized equation may be expressed generally as follows (normalized to a specific gravity of 1.030):

$$nu=u'=u \cdot (v/v')=u \cdot UVPRF=u \cdot SGF \quad (9)$$

The equation for nu (9) may be further normalized to adjust for a standard patient body weight such as of 70 kg or 154 lbs. This normalized value for nu may be reflected in the following equation:

$$nu=u'=u \cdot (v/v')=u \cdot SGF \cdot (WGT/K) \quad (10)$$

where WGT is equal to patient body weight, and K is a constant equal in this case to 154 lbs. It should be noted that this equation may be normalized to any reference value for specific gravity or weight.

Comparison of nu Value With Established Values

The normalized urine compliance marker concentration is then compared to established values for the patient. By obtaining multiple urine samples from a patient, once or twice a week, it is possible to establish an expected normalized compliance marker baseline against which a current or future value can be statistically compared. The expected normalized compliance marker baseline is the mean normalized compliance marker value from historical patient data. This method of monitoring compliance is dependent upon the assumption that the patient is initially compliant in order to get the expected value. In the alternative, expected ranges for normalized compliance marker concentrations from independent patient databases may be used for comparison. If any difference between calculated nu and expected nu is not explained by statistically acceptable deviation, then the patient is not in compliance. The actual medication dosage ingested may then be calculated as:

$$\frac{(\text{prescribed medication dose}) \cdot (\text{calculated } nu)}{\text{expected } nu}$$

Specific Examples and Supporting Data Using Method

Several methadone patients were independently prescribed diazepam for anxiety disorders. These patients were utilized to determine if it would be possible to compound a particular "marker" chemical in a set ratio to methadone such that one could tell how many doses of methadone each patient took. If the "marker" concentration in the urine satisfied specified statistical requirements as to the concentration level measured, then one would be sure that the patient did not ingest extra doses or divert methadone by not taking the full dose. These experiments were designed as follows:

Experiment #1 Query

Does normalized urine concentration of compliance marker correlate with doses of the underlying drug methadone given to patient?

Stages of Experiment #1

1. A fixed diazepam/methadone hydrochloride mixture ratio was chosen (1 mg diazepam per 15 mg methadone HCL). Methadone-marker solutions were prepared by adding sufficient diazepam liquid (10 mg/ml concentrate) to methadone concentrate (50 mg/ml) so as to manufacture unit samples containing either (4 mg diazepam/60 mg methadone) or (8 mg diazepam/120 mg methadone) such that the final volume (including water, color and flavor) of each dose was 15 ml.

2. To insure compliance with protocol for this experiment, three rehabilitated and compliant patients (each having been in methadone treatment for several years) were chosen for this experiment. Two patients ingested methadone 30 mg p.o. every 12 hours (half a bottle each time) and one patient ingested methadone 60 mg p.o. every 12 hours (half a bottle each time). On a random basis, each patient was asked to provide an observed urine sample for analysis prior to being given his or her daily dose. Each patient came to the office at least twice a week to pick up medication, ingest half their dose and be interviewed. Each experiment was conducted for a two month period. During this period, the only sources of methadone and diazepam available were given in the test site.

3. Diazepam was measured by FPIA normalized to a urine specific gravity of 1.030 and a total body weight of 154 lbs:

$$nu\ concentration=(u)\ (SCF)\ (wgt/154)$$

4. Results.

| PRESCRIBED MEDICATION | COMPLIANCE MARKER | MEAN NU FOR COMPLIANCE MARKER |
|---|---|---|
| P-1 methadone 30 mg p.o. q 12 h | diazepam 2 mg p.o. q 12 h | 500 (SD 90, CV 18%) |
| P-2 methadone 60 mg p.o. q 12 h | diazepam 4 mg p.o. q 12 h | 1068 (SD 233, CV 22%) |
| P-3 methadone 30 mg p.o. q 12 h | diazepam 2 mg p.o. q 12 h | 499 (SD 73, CV 15%) |

Expected ratio of marker P-1/marker P-3 should be 1.00; actual ratio observed was 1.00. Expected ratio of P-2/marker P-1 or P-3 should be 2.00; actual ratio was 2.13.

Experiment #2 Query

What happens if a patient were to ingest extra methadone from another source also containing compliance marker?

Stages of Experiment #2

1. For this experiment, patient P-3 was utilized. In order to simulate a patient ingesting twice as much methadone (underlying drug) each day (also with compliance marker), patient P-3 was given his standard methadone dose for several weeks prior to and following a one week change in the amount of compliance marker (2 mg diazepam per 15 mg methadone HCL) included in his normal 60 mg daily methadone dose so as to simulate "double dosing." Included in the following chart are sequential nu diazepam urine values for the pre-change period, simulation of "double dosing" and post-change period.

| Date: | marker status: | nu diazepam: |
|---|---|---|
| 02-19-96 | post-change | 534 ng/ml |
| 02-09-96 | post-change | 482 |
| 02-02-96 | post-change | 404 |
| 01-31-96 | post-change | 591 |
| 01-26-96 | double marker | 1163 |
| | | marker returned to 1 mg/15 mg methadone |
| 01-22-96 | double marker | 597 |
| 01-19-96 | pre-change | 450 |
| | | marker increased to 2 mg/15 mg methadone |
| 01-16-96 | pre-change | 519 |
| 01-03-96 | pre-change | 395 |

| Date: | marker status: | nu diazepam: |
|---|---|---|
| 12-29-95 | pre-change | 516 |
| 12-26-95 | pre-change | 344 |
| 12-22-95 | pre-change | 591 |

If the patient was "double dosing" one would expect to see (after about a week, since the average half-life of the diazepam metabolites is about 48 hours) at the end of a week, a compliance marker concentration about twice the baseline concentration. Expected concentration would be about 1000 ng/ml, while concentration observed was 1163 ng/ml. Therefore, if this patient had been non-compliant and getting methadone from another clinic, doctors would have been able to intervene.

Experiment #3 Query

What happens if a patient were to divert a portion of their daily doses?

Stages of Experiment #3

1. For this experiment, patient P-2 was utilized. In order to simulate a patient diverting half of her daily methadone (has take-homes with one clinic visit a week), a protocol similar to experiment #2 was done except compliance marker was decreased to 0.5 mg diazepam per 15 mg methadone HCL.

| Date: | marker status: | nu diazepam: |
|---|---|---|
| 02-09-96 | post-change | 1019 ng/ml |
| 02-06-96 | post-change | 1044 |
| 02-02-96 | post-change | 1073 |
| 01-30-96 | post-change | 1098 |
| 01-26-96 | half marker | 445 |
| | | increase marker to |
| | | 1 mg/15 mg methadone |
| 01-23-96 | half marker | 673 |
| 01-19-96 | half marker | 997 |
| | | decrease marker to |
| | | 0.5 mg/15 mg methadone |
| 01-16-96 | pre-change | 1044 |
| 01-12-96 | pre-change | 978 |
| 01-09-95 | pre-change | 1029 |
| 01-05-96 | pre-change | 896 |
| 01-02-96 | pre-change | 1210 |

If a patient were diverting half of their take-home doses, one would expect to see a decrease in the compliance marker concentration of half after a week or so. This is indeed what happened.

Experiment #4 Query

Figure 7:
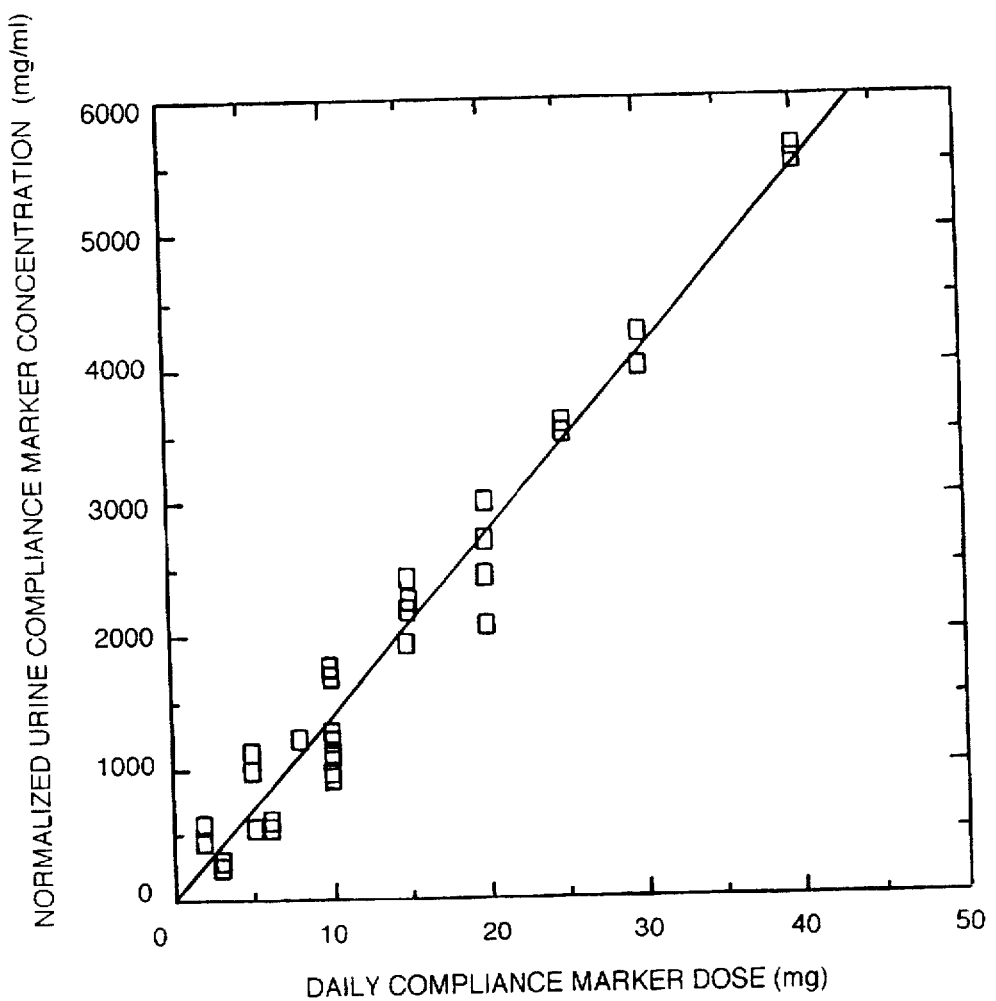
FIG. 7 is a graph of normalized urine compliance marker concentration versus daily compliance marker dose demonstrating their substantially linear relationship.

How to establish expected values for normalized urine compliance marker concentrations? Based on data gathered from over 50 patients observed over a four-year period, expected ranges for several normalized urine compliance marker concentrations have been established. For example, when diazepam is utilized as a compliance marker, the expected normalized value for urine diazepam-like immunoreactivity is 125 ng/ml/mg diazepam marker ingested. Statistical ranges for acceptable lows and highs have been established as being between 75 to 175 ng/ml/mg diazepam marker ingested. The linear correlation between normalized urine compliance marker concentration and daily compliance marker dose is illustrated in FIG. 7. Using preestablished data for normalized urine compliance marker concentration will eliminate the need to establish historical data bases for each individual patient.

It thus is seen that methods and compositions are now provided for monitoring patients who have been placed on medication maintenance programs or have been participants in experimental drug programs. The method utilizes a compliance marker concentration from evaluation of patient urine samples by FPIA to determine normalized urine compliance marker concentrations. Normalized urine compliance marker concentration can then be compared to an expected normalized urine compliance marker concentration. The actual drug dose ingested may then be calculated to determine compliance with the prescribed medication dose. The methods and compositions are clinically practical without high laboratory testing cost, the invasiveness of withdrawing blood, and the added exposure to medical professionals of patient blood having high probability of hepatitis and HIV infection. Furthermore, the methods and compositions do not require multiple equations to calculate normalized concentration values, or the consideration of numerous pharmacokinetics variables for each medication being monitored.

While this invention has been described in detail with particular references to preferred embodiments thereof, it should be understood that many modifications, additions and deletions may be made thereto, in addition to those expressly recited without departure from the spirit and scope of the invention as set forth in the following claims.

What is claimed is:

1. A method of monitoring compliance of a patient who has been placed on a medication maintenance program with a prescribed medication dosage, and with the method comprising the steps of:

(a) physically associating a compliance marker with a prescribed medication dosage prior to ingestion, (b) obtaining a sample of the patient's urine, (c) measuring the concentration of the compliance marker and its metabolites in the urine and the urine specific gravity, (d) calculating a normalized urine compliance marker and its metabolite concentration as a function of the measured compliance marker and its metabolite concentration in the urine and the urine specific gravity adjusted to account for the difference between the urine measured specific gravity and a preselected reference urine specific gravity, (e) comparing the normalized urine compliance marker and its metabolite concentration with an expected normalized urine compliance marker and its metabolite concentration for the amount of compliance marker prescribed, as an indication of compliance or non-compliance.

2. The method of claim 1 further including the step:

(f) calculating the amount of prescribed medication actually ingested by multiplying the prescribed medication dose with the calculated normalized urine compliance marker and its metabolite concentration, and dividing the product by the expected normalized urine compliance marker and its metabolite concentration.

3. A method of monitoring compliance of a patient who has been placed on a medication maintenance program with a prescribed medication dosage and having a compliance marker physically associated with the medication at a predetermined dosage, and with the method comprising the steps of:

(a) obtaining a sample of the patient's urine, (b) measuring the concentration of the compliance marker and its metabolites in the urine and the urine specific gravity, (c) calculating a normalized urine compliance marker and its metabolite concentration as a function of the measured compliance marker and its metabolite concentration in the urine and the urine specific gravity adjusted to account for the difference between the urine measured specific gravity and a preselected reference urine specific gravity.

(d) comparing the normalized urine compliance marker and its metabolite concentration with an expected normalized urine compliance marker and its metabolite concentration for the amount of compliance marker prescribed, as an indication of compliance or non-compliance.

4. The method of claim 3 further including the step:

(e) calculating the amount of prescribed medication actually ingested by multiplying the prescribed medication dose with the calculated normalized urine compliance marker and its metabolite concentration, and dividing the product by the expected normalized urine compliance marker and its metabolite concentration.

5. The method of claim 3 wherein step (c) the normalized urine compliance marker and its metabolite concentration is calculated in accordance with the equation $$nu = u \cdot SGF \cdot (WGT/K)$$

where nu is the normalized urine compliance marker and its metabolite concentration, u is the measured raw urine compliance marker and its metabolite concentration, SGF is the specific gravity factor of the urine sample calculated from the equation (rsg−1.000)/(msg−1.000), where rsg is the preselected reference urine specific gravity, and where msg is the urine measured specific gravity, where WGT is the patient body weight and K is a constant.

6. The method of claim 3 wherein step (b) the concentration of a benzodiazepine and its metabolites are measured.

7. The method of claim 6 wherein the benzodiazepine is diazepam.

8. The method of claim 6 wherein the benzodiazepine is alprazolam.

9. The method of claim 3 wherein step (b) the concentration of a barbiturate and its metabolites are measured.

10. The method of claim 9 wherein the barbiturate is phenobarbital.

11. A method of monitoring compliance of a patient who has been placed on a medication maintenance program with a prescribed medication dosage and having a compliance marker physically associated with the medication at a predetermined dosage, and with the method comprising the steps of:

(a) obtaining a sample of the patient's urine, (b) measuring the concentration of the compliance marker and its metabolites in the urine and the urine osmolality, (c) calculating a normalized urine compliance marker and its metabolite concentration as a function of the measured compliance marker concentration and its metabolite in the urine and the urine osmolality, (d) comparing the normalized urine compliance marker and its metabolite concentration with an expected normalized urine compliance marker and its metabolite concentration value prescribed, as an indication of compliance or non-compliance.

12. The method of claim 11 further including the step:

(e) calculating the amount of prescribed medication actually ingested by multiplying the prescribed medication dose with the calculated normalized urine compliance marker and its metabolite concentration, and dividing the product by the expected normalized urine compliance marker and its metabolite concentration.

13. The method of claim 11 wherein step (c) the normalized urine compliance marker and its metabolite concentration is calculated in accordance with the equation $$nu = u \cdot UOF \cdot (WGT/K)$$

where nu is the normalized urine compliance marker and its metabolite concentration, u is the measured raw urine compliance marker and its metabolite concentration, UOF is the urine osmolality factor of the urine sample defined as the ratio of the urine osmolality at a specific gravity of a reference urine sample to the urine osmolality equivalent at the actual urine specific gravity, where WGT is the patient body weight and K is a constant.

14. The method of claim 11 wherein step (b) the concentration of a benzodiazepine and its metabolites are measured.

15. The method of claim 14 wherein the benzodiazepine is diazepam.

16. The method of claim 14 wherein the benzodiazepine is alprazolam.

17. The method of claim 11 wherein step (b) the concentration of a barbiturate compliance marker and its metabolites are measured.

18. The method of claim 17 wherein the barbiturate is phenobarbital.

19. A method of claim 3 wherein step (b) the concentration of a weakly acidic medication and its metabolites are measured.

20. A method of claim 11 wherein step (b) the concentration of a weakly acidic medication and its metabolites are measured.

* * * * *